(12) United States Patent
Cornelius et al.

(10) Patent No.: US 6,344,481 B1
(45) Date of Patent: *Feb. 5, 2002

(54) THYROMIMETIC ANTIOBESITY AGENTS

(75) Inventors: Peter Cornelius, Old Lyme; Diane M. Hargrove, Ledyard; Bradley P. Morgan, Lyme; Andrew G. Swick, East Lyme, all of CT (US)

(73) Assignee: Pfizer Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/488,110

(22) Filed: Jan. 20, 2000

Related U.S. Application Data

(60) Provisional application No. 60/122,015, filed on Mar. 1, 1999.

(51) Int. Cl.⁷ .................. A61K 31/24; A61K 31/195; A61K 31/235

(52) U.S. Cl. .............. 514/539; 514/535; 514/563; 514/532

(58) Field of Search .................. 514/539, 535, 514/563, 532

(56) References Cited

U.S. PATENT DOCUMENTS

| | | | |
|---|---|---|---|
| 4,451,465 A | 5/1984 | White | 424/251 |
| 4,772,631 A | 9/1988 | Holloway | 514/539 |
| 4,977,148 A | 12/1990 | Holloway | 514/183 |
| 4,999,377 A | 3/1991 | Caulkett | 514/507 |
| 5,401,772 A | 3/1995 | Yokoyama | 514/539 |
| 5,569,674 A | 10/1996 | Yokoyama | 514/539 |
| 5,654,468 A | 8/1997 | Yokoyama | 560/43 |

FOREIGN PATENT DOCUMENTS

| | | | |
|---|---|---|---|
| JP | 50073948 A2 | * | 6/1975 |
| JP | 50124993 A2 | * | 10/1975 |
| JP | 54163937 A2 | * | 12/1979 |
| JP | 08034976 A2 | * | 2/1996 |

OTHER PUBLICATIONS

O'Connor et al. "Chemical additives in rumen fermentations. In vivo effects of two antiprotozoal compounds on rumen volatile fatty acids" J. Anim. Sci. (1971), 33(3), (abstract) pp. 662–666, 76:10723.*
Stephan, Z. F., et al, Atherosclerosis, 126, 53–63 (1996).

* cited by examiner

*Primary Examiner*—Theodore J. Criares
*Assistant Examiner*—Jennifer M Kim
(74) *Attorney, Agent, or Firm*—Peter C. Richardson; Gregg C. Benson; Carl J. Goddard

(57) ABSTRACT

The invention relates to pharmaceutical compositions and methods useful in the treatment of obesity which methods comprise administering to animal, including a human or companion animal, in need of such treatment an effective amount of a compound of the structural formula

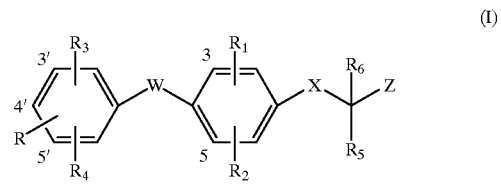

(I)

or a pharmaceutically acceptable salt, racemate or enantiomer thereof, wherein

R is hydroxy, esterified hydroxy or etherified hydroxy;

$R_1$ and $R_2$ are, independently, halogen, trifluoromethyl or lower alkyl;

$R_3$ is halogen, trifluoromethyl, lower alkyl, aryl, aryl-lower alkyl, cycloalkyl or cycloalkyl-lower alkyl, carbocyclic arylmethyl, carbocyclic aroyl, carbocyclic arylhydroxymethyl; or $R_3$ is the radical

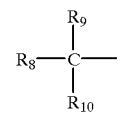

wherein $R_8$ is hydrogen, lower alkyl, aryl, cycloalkyl, aryl-lower alkyl or cycloalkyl-lower alkyl;

$R_6$ is hydroxy or acyloxy; $R_{10}$ is hydrogen or lower alkyl; or $R_9$ and $R_{10}$, taken together with the carbon atom to which they are attached, form a carbonyl group;

$R_4$ is hydrogen, halogen, trifluoromethyl or lower alkyl;

$R_5$ and $R_6$ are, independently, hydrogen or lower alkyl or $R_5$ and $R_6$, taken together with the carbon atom to which they are attached, form a carbonyl group;

X is O, S or —$NR_7$;

$R_7$ is hydrogen or lower alkyl;

W is O or S; and

Z is carboxyl or carboxyl derivatized as a pharmaceutically acceptable ester or amide.

The invention further provides for pharmaceutical compositions and methods of using the compounds of structural formula (I), or the pharmaceutically acceptable salts, racemates and enantiomers thereof, in combination with an anorectic agent, in treating obesity.

27 Claims, No Drawings

THYROMIMETIC ANTIOBESITY AGENTS

CROSS-REFERENCE TO RELATED APPLICATIONS

This application is filed claiming priority from U.S. Provisional Application No. 60/122,015, filed Mar. 1, 1999.

BACKGROUND OF THE INVENTION

This invention relates to pharmaceutical compositions and methods useful in treating obesity in animals, including mammalian subjects, particularly humans and companion animals.

Hitherto, the normal method employed in treating obesity has been reduction of caloric intake, either by a reduced calorie diet or through the use of appetite suppressants (anorectic agents), or a combination of the two. In general, the use of anorectic agents alone is not entirely satisfactory since they do not remain effective for the extended time periods that are necessary to achieve weight loss or they possess undesirable side-effects, particularly central stimulatory effects.

Alternatively, certain compounds have been disclosed that are able to induce weight loss by mechanisms other than appetite suppression, e.g. through stimulation of the peripheral metabolic rate of adipose tissue. For example, U.S. Pat. Nos. 4,451,465, 4,772,631, 4977,148 and 4,999,377 disclose compounds possessing thermogenic properties at dosages causing few or no deleterious side-effects, such as cardiac stimulation. The disclosures of U.S. Pat. Nos. 4,451,465, 4,772,631, 4,977,148 and 4,999,377 are incorporated herein by reference in their entirety. It is well-known to one of ordinary skill in the art that selectivity of thermogenic effect is an important requirement for a useful therapeutic agent in the treatment of, for example, obesity and related conditions.

The present invention provides methods for treating obesity which comprise administering to an animal, including a human or companion animal, in need of such treatment an obesity-treating amount of a compound of formula (I), or a pharmaceutically acceptable salt, racemate or enantiomer thereof, shown and defined hereinbelow.

The present invention further provides pharmaceutical compositions useful in the treatment of obesity which comprise an obesity-treating amount of a compound of formula (I), or a pharmaceutically acceptable salt, racemate or enantiomer thereof and an anorectic agent.

The compounds of formula (I), the pharmaceutically acceptable salts, racemates and enantiomers thereof, methods of preparing such compounds, salts, racemates and enantiomers and pharmaceutical compositions comprising such compounds, salts, racemates and enantiomers are disclosed in U.S. Pat. Nos. 5,401,772; 5,569,674 and 5,654,468, the disclosures of which are incorporated herein by reference.

In U.S. Pat. Nos. 5,401,772; 5,569,674 and 5,654,468 there is described a series of heteroacetic acid derivatives which are claimed to be useful in the treatment of occlusive cardiovascular conditions in which, inter alia, hyperlipidemia and hyperlipoproteinemia are implicated. Such conditions may include, for example, atherosclerosis, coronary heart disease and the like.

It has been subsequently disclosed in Stephan et al., Atherosclerosis, 126, 53–63 (1996) that a representative compound of these derivatives, ethyl N-[4-[3'-[(4-fluorophenyl)hydroxymethyl]-4'-hydroxyphenoxy]-3,5-dimethylphenyl]oxamate (CGS-26214), is devoid of both cardiovascular and thermogenic effects.

It has now been found that these heteroacetic acid derivatives, including CGS-26214, do, in fact, possess significant thermogenic properties. Accordingly, CGS-26214 and the compounds related thereto are useful in the treatment of obesity and related conditions.

SUMMARY OF THE INVENTION

This invention relates to methods for treating obesity which comprise administering to an animal, including a human or companion animal in need of such treatment, an obesity-treating amount of a compound of formula (I) or a pharmaceutically acceptable salt, racemate or enantiomer thereof, as shown and described hereinbelow. The administration of a compound of formula (I), or a pharmaceutically acceptable salt, racemate or enantiomer thereof, provides a thermogenic effect, that is thermogenesis is stimulated and, therefore, administration of the compound is of use in the treatment of obesity and conditions related thereto.

The invention is also directed to pharmaceutical compositions and methods of using such compositions in treating obesity in an animal, including a human or companion animal, which methods comprise administering to the animal in need of such treatment obesity-treating amounts of a compound of formula (I), or a pharmaceutically acceptable salt, racemate or enantiomer thereof, and an anorectic agent.

In a preferred aspect of the methods of this invention, the anorectic agent is selected from the group consisting of phenylpropanolamine, ephedrine, pseudoephedrine, phentermine, a Neuropeptide Y (hereinafter referred to as "NPY") antagonist, a cholecystokinin-A (hereinafter referred to as "CCK-A") agonist, a monoamine reuptake inhibitor, a sympathiomimetic agent, a serotoninergic agent, a dopamine agonist, a melanocyte-stimulating hormone receptor agonist or mimetic, a cannabinoid receptor antagonist, a melanocyte-stimulating hormone analog, a melanin concentrating hormone antagonist, the OB protein (hereinafter referred to as "leptin"), a leptin analog, a galanin antagonist and an orexin receptor antagonist. An especially preferred monoamine reuptake inhibitor is sibutramine, a preferred serotoninergic agent is dexfenfluramine or fenfluramine and a preferred dopamine agonist is bromocriptine.

The pharmaceutical compositions useful in treating obesity preferably comprise an amount of a compound of formula (I), or a pharmaceutically acceptable salt, racemate or enantiomer thereof, an anorectic agent and a pharmaceutically acceptable carrier or diluent.

The invention also relates to a kit comprising an amount of a compound of formula (I), or a pharmaceutically acceptable salt, racemate or enantiomer thereof, and a pharmaceutically acceptable carrier or diluent in a first unit dosage form, an amount of an anorectic agent and a pharmaceutically acceptable carrier or diluent in a second unit dosage form and a container.

DETAILED DESCRIPTION OF THE INVENTION

According to the instant invention, there are provided pharmaceutical compositions and methods useful for treating obesity in mammals, including humans and companion animals, which methods comprise administering to a mammal in need of such treatment an obesity-treating amount of a compound of the formula

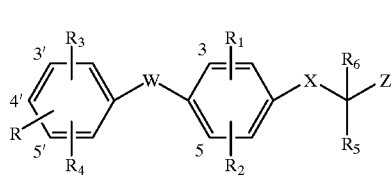 (I)

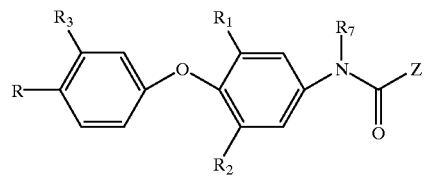 (II)

or a pharmaceutically acceptable salt, racemate or enantiomer thereof, wherein

R is hydroxy, esterified hydroxy or etherified hydroxy;

$R_1$ and $R_2$ are, independently, halogen, trifluoromethyl or lower alkyl;

$R_3$ is halogen, trifluoromethyl, lower alkyl, lower alkanoyl, hydroxy-lower alkyl, aryl, aryl-lower alkyl, cycloalkyl or cycloalkyl-lower alkyl, carbocyclic arylmethyl, carbocyclic aroyl, carbocyclic arylhydroxymethyl; or $R_3$ is the radical

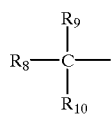

wherein $R_8$ is hydrogen, lower alkyl, aryl, cycloalkyl, aryl-lower alkyl or cycloalkyl-lower alkyl;

$R_9$ is hydroxy or acyloxy; $R_{10}$ is hydrogen or lower alkyl; or $R_9$ and $R_{10}$, taken together with the carbon atom to which they are attached, form a carbonyl group;

$R_4$ is hydrogen, halogen, trifluoromethyl or lower alkyl;

$R_5$ and $R_6$ are, independently, hydrogen or lower alkyl or $R_5$ and $R_6$, taken together with the carbon atom to which they are attached, form a carbonyl group;

X is O, S or —$NR_7$;

$R_7$ is hydrogen or lower alkyl;

W is O or S and

Z is carboxyl or carboxyl derivatized as a pharmaceutically acceptable ester or amide.

Generally preferred embodiments of the pharmaceutical compositions and methods of the instant invention relate to the use of compounds of formula (I) and the pharmaceutically acceptable salts, racemates and enantiomers thereof wherein R is located at the 4'-position; $R_1$ and $R_2$ are located at the 3 and 5 positions; $R_3$ and $R_4$ are located at the 3' and 5-positions; X is O or —$NR_7$, W is O; $R_4$ is hydrogen and Z is carboxyl or carboxyl derivatized as a pharmaceutically acceptable ester.

A preferred embodiment of the compositions and methods of this invention relates to the use of a subgroup of compounds of formula (I) having the formula (II):

or the pharmaceutically acceptable salts, racemates or enantiomers thereof, wherein R is hydroxy, esterified hydroxy or etherified hydroxy;

$R_1$ and $R_2$ are, independently, halogen, trifluoromethyl or $(C_1-C_3)$alkyl;

$R_3$ is lower alkyl, lower alkanoyl, hydroxy-lower alkyl, carbocyclic arylmethyl, carbocyclic aroyl or carbocyclic aryl hydroxymethyl;

$R_7$ is hydrogen or lower alkyl and

Z represents carboxyl or carboxyl derivatized as a pharmaceutically acceptable ester or amide.

A further preferred embodiment of the compositions and methods of this invention relates to the use of yet another subgroup of compounds of formula (I) having the formula (III):

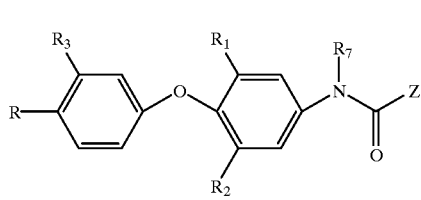 (III)

or the pharmaceutically acceptable salts, racemates or enantiomers thereof, wherein R is hydroxy, esterified hydroxy or etherified hydroxy;

$R_1$ and $R_2$ are, independently, halogen, trifluoromethyl or $(C_1-C_3)$alkyl;

$R_3$ is lower alkyl, carbocyclic aroyl, carbocyclic arylmethyl or carbocyclic aryl hydroxymethyl;

$R_7$ is hydrogen or lower alkyl and

Z represents carboxyl or carboxyl derivatized as a pharmaceutically acceptable ester or amide.

Preferred compounds for use in the pharmaceutical compositions and methods of this invention include those compounds of formula (III), and the pharmaceutically acceptable salts, racemates and enantiomers thereof, wherein R is hydroxy, acyloxy, lower alkanoyloxy, lower alkoxy or tetrahydropyranyloxy; $R_1$ and $R_2$ are the same and are halogen or $(C_1-C_3)$alkyl; $R_3$ is $(C_1-C_3)$alkyl or monocyclic carbocyclic arylmethyl; $R_7$ is hydrogen or $(C_1-C_2)$alkyl and Z is carboxyl or carboxyl derivatized as a pharmaceutically acceptable ester or amide.

Further preferred compounds for use in the pharmaceutical compositions and methods of this invention include those compounds of formula (III), and the pharmaceutically acceptable salts, racemates and enantiomers thereof, wherein R is hydroxy; $R_1$ and $R_2$ are the same and are chloro or methyl; $R_3$ is isopropyl, benzyl or benzyl substituted by halogen, lower alkyl, lower alkoxy or trifluoromethyl; $R_7$ is hydrogen and Z is carboxyl or lower alkoxycarbonyl.

Another preferred embodiment of the instant invention includes compounds of structural formula (III), or the pharmaceutically acceptable salts, racemates or enantiomers thereof, wherein R is hydroxy, lower alkanoyloxy, lower alkoxy or tetrahydropyranyloxy; $R_1$ and $R_2$ are, independently, halogen or $(C_1-C_3)$alkyl; $R_3$ is carbocyclic aroyl or carbocyclic aryl hydroxymethyl; $R_7$ is hydrogen or $(C_1-C_2)$alkyl and Z is carboxyl or carboxyl derivatized as a pharmaceutically acceptable ester or amide.

Yet another preferred grouping of compounds of formula (III), including the pharmaceutically acceptable salts, racemates and enantiomers thereof, are those wherein R is hydroxy; $R_1$ and $R_2$ are the same and are chloro or methyl; $R_3$ is phenyl-hydroxymethyl, phenyl-hydroxymethyl substituted on phenyl by halogen, lower alkyl, lower alkoxy or trifluoromethyl or benzoyl or benzoyl substituted by halogen, lower alkyl, lower alkoxy or trifluoromethyl; $R_7$ is hydrogen and Z is carboxyl or lower alkoxycarbonyl.

Especially preferred compounds of formula (I), including the pharmaceutically acceptable salts, racemates and enantiomers thereof, which are useful in the pharmaceutical compositions and methods of the instant invention are N-[3,5-dimethyl-4-(4'-hydroxy-3'-isopropylphenoxy)-phenyl]-oxamic acid (CGS-23425), N-[3,5-dichloro-4-(4'-hydroxy-3'-isopropylphenoxy)-phenyl]-oxamic acid, ethyl N-[4-[3'-[(4-fluorophenyl)hydroxymethyl]-4'-hydroxyphenoxy]-3,5dimethylphenyl]oxamate (CGS-26214) and N-[4-[3'-[(4-fluorophenyl)hydroxymethyl]-4'-hydroxyphenoxy]-3,5-dimethylphenyl]oxamic acid.

Certain compounds employed in the pharmaceutical compositions and methods of this invention may have one or more asymmetric centers and can exist in the form of racemates, and enantiomers thereof, all of which are intended to be included within the spirit and scope of the invention.

Unless otherwise provided, the chemical nomenclature employed herein have the following meanings within the scope of the present invention.

Aryl represents carbocyclic or heterocyclic aryl.

Carbocyclic aryl represents optionally substituted phenyl or optionally substituted naphthyl.

Optionally substituted phenyl represents preferably phenyl or phenyl substituted by one to three substituents, preferably lower alkyl, hydroxy, lower alkoxy, lower alkanoyloxy, halogen, cyano, trifluoromethyl, lower alkanoylamino or lower alkoxycarbonyl.

Optionally substituted naphthyl represents 1- or 2-naphthyl or 1- or 2-naphthyl preferably substituted by lower alkyl, lower alkoxy or halogen.

Heterocyclic aryl is preferably monocyclic heterocyclic aryl such as optionally substituted thienyl, furanyl, pyridyl, pyrrolyl or N-lower alkylpyrrolyl.

Optionally substituted furanyl represents 2- or 3-furanyl or 2- or 3-furanyl preferably substituted by lower alkyl.

Optionally substituted pyridyl represents 2-, or 3- or 4-pyridyl or 2-, or 3- or 4-pyridyl preferably substituted by lower alkyl or halogen.

Optionally substituted thienyl represents 2- or 3-thienyl or 2- or 3-thienyl preferably substituted by lower alkyl.

Aryl as employed in the term "aryl-lower" and the like is preferably phenyl or phenyl substituted by one or two of lower alkyl, lower alkoxy, hydroxy, lower alkanoyloxy, halogen, trifluoromethyl, cyano, lower alkanoylamino or lower alkoxycarbonyl.

Aryl-lower alkyl is benzyl or phenethyl optionally substituted by one or two of lower alkyl, lower alkoxy, hydroxy, lower alkanoyloxy, halogen or trifluoromethyl.

The term "lower" as employed herein in connection with compounds or organic radicals defines such compounds or radicals with up to and including seven, preferably up to and including four and, more preferably, one or two carbon atoms, including branched or straight-chain configurations thereof.

A lower alkyl group preferably contains from one to four carbon atoms and represents, for example, methyl, ethyl, propyl or butyl.

A lower alkoxy group preferably contains from one to four carbon atoms and is, for example, methoxy, ethoxy, propoxy, isopropoxy or butoxy.

Cycloalkyl is a saturated cyclic hydrocarbon radical, preferably a $C_5$ to $C_7$ cycloalkyl radical which contains five to seven ring carbons and is, preferably, cyclopentyl or cyclohexyl.

Cycloalky-lower alkyl is preferably 1- or 2-(cyclopentyl or cyclohexyl)ethyl, 1-, 2- or 3-(cyclopentyl or cyclohexyl) propyl, or 1-, 2-, 3- or 4-(cyclopentyl- or cyclohexyl)butyl.

Lower alkenyloxy represents preferably allyloxy.

Di-lower alkylamino preferably contains one to four carbon atoms in each lower alkyl portion and is, for example, N,N-dimethylamino, N-methyl-N-ethyamino and N,N-diethylamino.

Lower alkoxycarbonyl preferably contains one to four carbon atoms in the alkoxy moiety and is, for example, methoxycarbonyl, ethoxycarbonyl, propoxycarbonyl and isopropoxycarbonyl.

Hydroxy-lower alkyl is preferably hydroxymethyl.

Halogen (halo) preferably represents fluoro or chloro, but may also be bromo or iodo.

Lower alkanoyl is preferably acetyl, propionyl, butyryl or pivaloyl.

Lower alkanoyloxy is preferably acetoxy, propionyloxy or pivaloyloxy.

Acylamino is preferably lower alkanoylamino, aroylamino or aryl-lower alkoxycarbonylamino, such as benzyloxycarbonylamino.

Lower alkanoylamino is preferably acetamido or propionamido.

Aroyl is preferably benzoyl or benzoyl substituted on the benzene ring by lower alkyl, lower alkoxy, halogen or trifluoromethyl.

Acyl is preferably lower alkanoyl, carbocyclic aryl-lower alkanoyl or carbocyclic aroyl.

Carboxyl derivatized as a pharmaceutically acceptable ester is esterified carboxyl, preferably a prodrug ester convertible by solvolysis or under physiological conditions to the free carboxylic acid, such as being preferably lower alkoxycarbonyl; (amino, acylamino, mono- or di-lower alkylamino)-lower alkoxycarbonyl; carboxy-lower alkoxycarbonyl, e.g. α-carboxy-lower alkoxycarbonyl; lower alkoxycarbonyl-lower alkoxycarbonyl, e.g. α-lower alkoxycarbonyl-lower alkoxycarbonyl; α-(di-lower alkylamino, amino, mono-lower alkylamino, morpholino, piperidino, pyrrolidino, 1-lower alkyl-piperazino)-carbonyl-lower alkoxycarbonyl; carbocyclic or heterocyclic aryl-lower alkoxycarbonyl, preferably optionally (halogen, lower alkyl or lower alkoxy)-substituted benzyloxycarbonyl, or pyridylmethoxycarbonyl; 1-(hydroxy, lower alkanoyloxy or lower alkoxy)-lower alkoxycarbonyl, e.g. pivaloyloxymethoxycarbonyl; (hydroxy, lower alkanoyloxy or lower alkoxy)lower alkoxymethoxycarbonyl; 1-(lower alkoxycarbonyloxy)-lower alkoxycarbonyl; 5-indanyloxycarbonyl; 3-phthalidoxycarbonyl and (lower alkyl, lower alkoxy or halogen)-substituted 3-phthalidoxycarbonyl; dihydroxypropyloxycarbonyl wherein hydroxy groups are free or are protected in the form of ketals, e.g. a lower alkylidene, a benzylidene or a 5- or 6-membered cycloalkylidene derivative, preferably being (2,2-dimethyl-1,3-dioxolan-4-yl)-methoxycarbonyl.

Carboxyl derivatized as a pharmaceutically acceptable prodrug ester is preferably $(C_1-C_4)$alkoxycarbonyl, benzyloxycarbonyl, optionally substituted on phenyl by lower alkyl, lower alkoxy, halogen, or trifluoromethyl, 1-$(C_2-C_4$-alkanoyloxy)-methoxycarbonyl, (2,2-dimethyl-1, 3-dioxolan-4-yl)-methoxycarbonyl, 5-indanyloxycarbonyl, 1 -$(C_1-C_4$-alkoxycarbonyloxy)-ethoxycarbonyl or 3-pyridylmethoxycarbonyl.

Carboxyl derivatized as a pharmaceutically acceptable amide is preferably carbamoyl or N-substituted carbamoyl, preferably lower alkylamino, arylamino, di-lower alkylamino, morphlino, N-lower alkylpiperazino, pyrrolidino, piperidino, (amino or acylamino)-lower alkylamino or aryl-lower alkylamino]-carbonyl.

Esterified hydroxy is acyloxy, e.g. acyloxy derived from an organic carboxylic acid, preferably lower alkanoyloxy, aroyloxy, or aryl-lower alkanoyloxy; also 3,7,12-$(3\alpha,5\beta,7\alpha, 12\alpha)$-trihydroxy-cholan-24-oyloxy (derived from cholic acid), and the like.

Etherified hydroxy is preferably lower alkoxy, lower alkenyloxy, $(C_5-C_7)$-cycloalkyloxy, carbocyclic aryl-lower alkoxy, tetrahydropyranyloxy, $(C_5-C_7)$-cycloalkyl-lower alkoxy, and the like.

The term "animal" is meant to embrace both companion animals and humans. In this regard, the phrase "companion animal" is meant to embrace a household pet or other domesticated animal including, but not limited to, cattle, sheep, ferrets, swine, horses, poultry, fish, rabbits, goats, dogs, cats and the like. Particularly preferred companion animals are dogs and cats.

Pharmaceutically acceptable salts are either pharmaceutically acceptable acid addition salts for any basic compounds used in the pharmaceutical compositions and methods of this invention or salts derived from pharmaceutically acceptable bases for any acidic compounds used in the pharmaceutical compositions and methods of this invention.

Pharmaceutically acceptable salts of the basic compounds used in the pharmaceutical compositions and methods of this invention are acid addition salts, which are preferably therapeutically acceptable inorganic or organic acids, such as strong mineral acids, for example, hydrohalic, e.g. hydrochloric, hydrobromic, sulfuric or phosphoric acid; aliphatic or aromatic carboxylic or sulphonic acids, e.g. acetic, propionic, succinic, gylcollic, lactic, malic, tartaric, gluconic, citric, maleic, fumaric, pyruvic, phenylacetic, benzoic, pamoic, nicotinic, methanesulfonic, ethanesulfonic, hydroxyethanesulfonic, 1,2-ethanedisulfonic, benzenesulfonic, p-toluenesulfonic or naphthalenesulfonic acid or ascorbic acid.

Pharmaceutically acceptable salts of the acidic compounds used in the pharmaceutical compositions and methods of this invention, e.g. those compounds having a carboxyl group, are salts formed with pharmaceutically acceptable bases, e.g. alkali metal salts (sodium, potassium salts), alkaline earth metal salts (magnesium, calcium salts), amine salts (ethanolamine, diethanolamine, triethanolamine, trimethamino salts).

The compounds of formula (I), including the pharmaceutically acceptable salts, racemates and enantiomers thereof and the preferred embodiments related thereto employed in the pharmaceutical compositions and methods of the instant invention, may be readily prepared according to the teachings in the aforementioned U.S. Pat. Nos. 5,401,772; 5,569, 674 and 5,654,468.

One aspect of the instant invention is directed to methods of treating obesity in an animal, including a human or companion animal, which comprise administering to an animal in need of such treatment an obesity-treating amount of a compound of formula (I), or a pharmaceutically acceptable salt, racemate or enantiomer thereof.

When treating obesity, generally satisfactory results are obtained when a compound of formula (I) or a pharmaceutically acceptable salt, racemate or enantiomer thereof, is administered to an animal, including a human or companion animal, either orally, parenterally or transdermally. Administration by the oral route is normally preferred, being more convenient and avoiding the possible pain and irritation of injection. However, in circumstances where the subject cannot ingest the medication or absorption following oral administration is impaired, as by disease or other abnormality, it is essential that the compound be administered parenterally or transdermally.

By any route of administration, the dosage of the compound of formula (I), or the pharmaceutically acceptable salt, racemate or enantiomer thereof, is in the range of from about 0.005 to about 100 mg/kg body weight of the subject per day, preferably about 0.3 to about 50 mg/kg body weight of the subject per day and most preferably about 1 to about 10 mg/kg body weight of the subject per day, preferably administered singly or as a divided dose.

In a preferred aspect of the methods of this invention, the compound of formula (I) is N-[3,5-dimethyl-4-(4'-hydroxy-3'-isopropylphenoxy)-phenyl]-oxamic acid (CGS-23425) or a pharmaceutically acceptable salt thereof; N-[3,5-dichloro-4-(4'-hydroxy-3'-isopropylphenoxy)-phenyl]-oxamic acid or a pharmaceutically acceptable salt thereof; ethyl N-[4-[3'-[(4-fluorophenyl)hydroxymethyl]'-hydroxyphenoxy]-3,5-dimethylphenyl]oxamate (CGS-26214) or a racemate or enantiomer thereof or N-[4-[3'-[(4-fluorophenyl) hydroxymethyl]4'-hydroxyphenoxy]-3,5-dimethylphenyl] oxamic acid, or a pharmaceutically acceptable salt, racemate or enantiomer thereof.

The instant invention is also directed to methods of treating obesity in animal which comprise administering to an animal, including a human or companion animal, in need of such treatment obesity-treating amounts of a combination comprising a compound of formula (I), or a pharmaceutically acceptable salt, racemate or enantiomer thereof, and an anorectic agent.

The administration of the compound of formula (I) and the anorectic agent according to this invention can be sequential in time or simultaneous with the simultaneous method being generally preferred. For sequential administration, the compound of formula (I) and the anorectic agent can be administered in any order. It is generally preferred that such administration be oral. It is even more preferred that the administration be oral and simultaneous. However, if the subject being treated is unable to swallow, or oral absorption is otherwise impaired or undesirable, parenteral or transdermal administration will be appropriate. When the compound of formula (I) and the anorectic agent are administered sequentially, the administration of each can be by the same method or by different methods.

In a preferred aspect of the methods of this invention, the anorectic agent is selected from the group consisting of phenylpropanolamine, ephedrine, pseudoephedrine, phentermine, a Neuropeptide Y (hereinafter referred to as "NPY") antagonist, a cholecystokinin-A (hereinafter referred to as "CCK-A") agonist, a monoamine reuptake inhibitor, a sympathiomimetic agent, a serotoninergic agent, a dopamine agonist, a melanocyte-stimulating hormone receptor agonist or mimetic, a cannabinoid receptor antagonist, a melanocyte-stimulating hormone analog, a melanin concentrating hormone antagonist, the OB protein (hereinafter referred to as "leptin"), a leptin analog, a galanin antagonist and an orexin receptor antagonist. Such classes of anorectic agents are, or will be, well known to one of ordinary skill in the art.

In yet another preferred aspect of the methods of this invention, the compound of formula (I) is N-[3,5-dimethyl-4-(4'-hydroxy-3'-isopropylphenoxy)-phenyl]-oxamic acid (CGS-23425) or a pharmaceutically acceptable salt thereof; N-[3,5-dichloro-4-(4'-hydroxy-3'-isopropylphenoxy)-phenyl]-oxamic acid or a pharmaceutically acceptable salt thereof; ethyl N-[4-[3'-[(4-fluorophenyl)hydroxymethyl]-4'-hydroxyphenoxy]-3,5-dimethylphenyl]oxamate (CGS-26214) or a racemate or enantiomer thereof or N-[4-[3'-[(4-fluorophenyl)hydroxymethyl]-hydroxyphenoxy]-3,5-dimethylphenyl]oxamic acid or a pharmaceutically acceptable salt, racemate or enantiomer thereof, and the anorectic agent is selected from the group consisting of a CCK-A agonist, leptin, a leptin analog and a galanin antagonist.

In an especially preferred aspect of the methods of this instant invention, the anorectic agent is phentermine, the monoamine reuptake inhibitor is sibutramine, the serotoninergic agent is dexfenfluramine or fenfluramine and the dopamine agonist is bromocriptine.

The preferred anorectic agent phentermine may be prepared as described in U.S. Pat. No. 2,408,345, the disclosure of which is incorporated herein by reference.

The preferred monoamine reuptake inhibitor sibutramine can be prepared as described in U.S. Pat. No. 4,929,629, the disclosure of which is incorporated herein by reference.

The preferred serotoninergic agents fenfluramine and dexfenfluramine can be prepared as described in U.S. Pat. No. 3,198,834, the disclosure of which is incorporated herein by reference.

The preferred dopamine agonist bromocriptine can be prepared as described in U.S. Pat. Nos. 3,752,814 and 3,752,888, the disclosures of which are incorporated herein by reference.

When treating obesity, generally satisfactory results are obtained when the combination of the instant invention, i.e. a compound of structural formula (I) or a pharmaceutically acceptable salt, racemate or enantiomer thereof, together with an anorectic agent is administered to an animal, including a human or a companion animal, either orally, parenterally or transdermally. Administration by the oral route is normally preferred, being more convenient and avoiding the possible pain and irritation of injection. However, in circumstances where the subject cannot ingest the medication or absorption following oral administration is impaired, as by disease or other abnormality, it is essential that the drug be administered parenterally or transdermally.

By any route of administration, the dosage of the compound of formula (I) or the pharmaceutically acceptable salt, racemate or enantiomer thereof, is in the range of from about 0.005 to about 100 mg/kg body weight of the subject per day, preferably from about 0.3 to about 50 mg/kg body weight of the subject per day and most preferably from about 1 to about 10 mg/kg body weight of the subject per day, preferably administered singly or as a divided dose.

The dosage of the anorectic agent is generally in the range of from about 0.01 to about 50 mg/kg body weight of the subject per day, preferably from about 0.1 to about 10 mg/kg body weight of the subject per day, administered singly or as a divided dose.

When the anorectic agent is phentermine, the dosage of phentermine is from about 0.01 to 10 mg/kg body weight of the subject per day, preferably from about 0.1 to about 1 mg/kg body weight of the subject per day.

When the anorectic agents is sibutramine, the dosage range is from about 0.01 to about 30 mg/kg body weight of the subject per day, preferably from about 0.1 to about 1 mg/kg body weight of the subject per day.

When the anorectic agent is dexfenfluramine or fenfluramine, the dosage range is from about 0.01 to about 30 mg/kg body weight of the subject per day, preferably from about 0.01 to about 1 mg/kg body weight of the subject per day.

When the anorectic agent is bromocriptine, the dosage range is from about 0.01 to about 10 mg/kg body weight of the subject per day, preferably from about 0.1 to about 10 mg/kg body weight of the subject per day.

It will be appreciated that, when treating an animal according to the methods of the instant invention, the actual preferred route of administration and optimum dosage utilized will be at the sound professional discretion of the person responsible for the treatment and may vary according to the severity of the condition to be treated, the intended route of administration and patient characteristics such as age, weight, rate of excretion, concurrently administered medications and general physical condition of the subject. Normally, the optimum dosage for the subject being treated will be determined by generally administering smaller doses initially and thereafter incrementally modifying the regimen, if required, to determine the most suitable dosage. This may vary according to the particular compound employed and with the nature of the subject being treated.

The compounds of formula (I), the pharmaceutically acceptable salts, racemates and enantiomers thereof, and combinations thereof with anorectic agents, are preferably administered in the form of a pharmaceutical composition comprising a pharmaceutically acceptable carrier or diluent. Accordingly, the compounds of formula (I), the pharmaceutically acceptable salts, racemates and enantiomers thereof, and combinations thereof with anorectic agents, can be administered individually or together in any conventional oral, parenteral or transdermal dosage form.

Suitable pharmaceutically-acceptable carriers include inert solid fillers or diluents and sterile aqueous or organic solutions. The active compounds will be present in such pharmaceutical compositions in amounts sufficient to provide the desired dosage amount in the range described above. Thus, for oral administration, the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These pharmaceutical compositions may also be administered parenterally. For parenteral administration the pharmaceutical compositions can be combined with sterile aqueous or organic media to form injectable solutions or suspensions. Solutions or suspensions of these pharmaceutical compositions can be prepared in water suitably mixed with a surfactant such as hydroxypropylcellulose. Dispersions can also be prepared in sesame or peanut oil, ethanol, water, polyol (e.g., glycerol, propylene glycol and liquid polyethylene glycol), suitable mixtures thereof, vegetable oils, N-methyl glucamine, polyvinylpyrrolidone and mixtures thereof in oils as well as aqueous solutions of water-soluble pharmaceutically acceptable salts of the compounds. Under ordinary conditions of storage and use, these preparations contain a preservative to prevent the growth of microorganisms. The injectable solutions prepared in this manner can then be administered intravenously, intraperitoneally, subcutaneously, or intramuscularly, with intramuscular administration being the preferred parenteral route in humans.

The pharmaceutical forms suitable for injectable use include sterile aqueous solutions or dispersions and sterile powders for the preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi.

The pharmaceutical compositions may also be administered transdermally. Suitable formulations for transdermal application include an obesity-treating amount of a compound or pharmaceutical composition of the invention with a suitable transdermal carrier. Preferred transdermal carriers include absorbable pharmacologically acceptable solvents to promote and assist passage through the skin of the subject being treated. Characteristically, transdermal devices comprise the form of a bandage having a backing member, a reservoir containing the compound, optionally with carriers, optionally a rate-controlling barrier to deliver the compound to the skin of the subject being treated at a controlled and predetermined rate over a prolonged period of time and means to secure the device to the skin of the subject being treated.

Methods of preparing the various pharmaceutical compositions with a desired amount of an active ingredient or ingredients are known, or will be apparent in light of this disclosure, to one of ordinary skill in the art. See, for example, Remington's Pharmaceutical Sciences, Mack Publishing Company, Easton, Pa., 15th Edition (1975).

As a consequence of their thermogenic actions, the methods and pharmaceutical compositions of the instant invention also have utility in the treatment of obesity in companion animals, preferably dogs and cats. The administration of the pharmaceutical compositions of this invention may be effected orally, parenterally or transdermally. An amount of a pharmaceutical composition of the invention is administered such that an effective dose is received, normally a daily dose, as set forth hereinabove.

Conveniently, the medicaments can be carried in the drinking water such that a therapeutic dosage of the agents is ingested with the daily water supply. The agents can be directly metered into drinking water, preferably in the form of a liquid, water-soluble concentrate, such as an aqueous solution of a water-soluble salt.

For purposes of alternative convenience, the active ingredients can also be added directly to the companion animal's feed, as such, or in the form of an animal feed supplement, also referred to as a premix or concentrate. A premix or concentrate of the therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and various mineral mixes. A particularly effective carrier is the respective animal feed itself, i.e., a small portion of such feed. The carrier facilitates uniform distribution of the active materials in the finished feed with which the premix is blended. It is important that the compounds be thoroughly blended into the premix and, subsequently, the feed. In this respect, the agents may be dispersed or dissolved in a suitable oily vehicle such as soybean oil, corn oil, cottonseed oil, and the like, or in a volatile organic solvent and then blended with the carrier. It will be appreciated that the proportions of active materials in the concentrate are capable of wide variation since the amount of agent in the finished feed may be adjusted by blending the appropriate proportion of premix with the feed to obtain a desired level of the therapeutic agents.

High potency concentrates may be blended by the feed manufacturer with a proteinaceous carrier such as soybean oil meal and other meals, as described above, to produce concentrated supplements which are suitable for direct feeding to animals. In such instances, the animals are permitted to consume the usual diet Alternatively, such concentrated supplements may be added directly to the feed to produce a nutritionally balanced, finished feed containing a therapeutically effective level of a compound according to this invention. The mixtures are thoroughly blended by standard procedures, such as in a twin shell blender, to insure homogeniety. If the supplement is used as a top dressing for the feed, it likewise helps to insure uniformity of distribution of the active ingredient across the top of the dressed feed.

For veterinary uses, both paste and pellet formulations may also be conveniently employed. Paste formulations can be prepared readily by dispersing the active compounds in a pharmaceutically acceptable oil such as peanut oil, sesame oil, corn oil, and the like. Similarly, pellets containing an effective amount of the compounds of the instant invention can be prepared by admixing the compounds of this invention with a suitable diluent such as carbowax, carnuba wax, and the like, and a lubricant, such as magnesium or calcium stearate, can be employed to improve the pelleting process.

Since the instant invention relates to the treatment of obesity with a combination of active ingredients which may be administered separately, the invention also relates to combining separate pharmaceutical compositions in kit form. A kit, according to this invention, comprises two separate pharmaceutical compositions: a first unit dosage form comprising a compound of formula (I), or a pharmaceutically acceptable salt, racemate or enantiomer thereof, and a pharmaceutically acceptable carrier or diluent and a second unit dosage form comprising an anorectic agent and a pharmaceutically acceptable carrier or diluent. The kit further comprises a container. The container is used to contain the separate pharmaceutical compositions and may comprise, for example, a divided bottle or a divided foil packet, however, the separate pharmaceutical compositions may also be contained within a single, undivided container. Normally, the kit will also include directions for the administration of the separate components. The kit form is particularly advantageous when the separate components are preferably administered in different dosage forms (e.g., oral and parenteral), are administered at different dosage levels, or when titration of the individual components of the combination is desired by the prescribing physician.

One example of such a kit comprises a so-called blister pack. Blister packs are well known in the packaging industry and are being used widely for the packaging of pharmaceutical unit dosage forms (tablets, capsules and the like). Blister packs generally comprise a sheet of relatively rigid material covered with a foil of a preferably transparent plastic material. During the packaging process recesses are formed in the plastic foil. The recesses generally conform to the size and shape of the tablets or capsules to be contained therein. Next, the tablets or capsules are placed in the recesses and the sheet of relatively rigid material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules may be removed from the blister pack by the application of manual pressure on the recesses whereby an opening is formed in the sheet at the place of the recess. The tablet or capsule can then be removed through the formed opening.

It is further desirable to provide a memory aid on the pack, e.g., in the form of numbers or similar indicia next to the tablets or capsules whereby the indicia correspond with the days of the regimen which the dosage form so specified is to be ingested. An additional example of such a memory aid is a calendar printed on the pack, e.g., as follows "First Week, Monday, Tuesday, . . . etc. . . Second Week, Monday, Tuesday, . . . "etc. Other variations will be readily apparent. A "daily dose" can be a single tablet or capsule or multiple tablets or capsules to be ingested on a given day. Also, a daily dose comprising a compound of formula (I), or a pharmaceutically acceptable salt, racemate or enantiomer thereof, can consist of one tablet or capsule while a daily dose comprising an anorectic agent can consist of multiple tablets or capsules, or vice versa. The memory aid should reflect this.

In another specific embodiment of the invention, a pack designed to dispense the daily doses one at a time in the order of their intended use is provided. Preferably, the pack is equipped with a memory aid, so as to further facilitate compliance with the dosage regimen. An example of such a memory aid is a mechanical counter which indicates the number of daily doses to be dispensed. Another example of such a memory aid is a battery-powered micro-chip memory coupled with a liquid crystal readout, or audible reminder signal which, for example, reads out the date that the last daily dose has been taken and/or reminds the patient when the next dose is to be taken.

EXPERIMENTAL

The consumption of oxygen by animals to produce heat is a principle well known to one of ordinary skill in the art. See, for example, M. Kleiber, "The Fire of Life", Robert E. Krieger Pub. Co., New York, N.Y., 1975.

During increased energy expenditure, metabolic fuels, e.g. glucose or fatty acids, are oxidized to $CO_2$ and $H_2O$ with concomitant evolution of heat, i.e. thermogenesis. Thus, the measurement of oxygen consumption in animals, including humans and companion animals, is an indirect measure of thermogenetic effect. In this regard, indirect calorimetry has been demonstrated to be a valid method for the measurement of energy expenditure and has been employed extensively in animals, including humans.

The ability of the compounds of formula (I), their pharmaceutically acceptable salts, racemates and enantiomers thereof, to generate a thermogenic response and, therefore, to have utility in the treatment of obesity is demonstrated in the following protocol.

This in vivo screen is designed to evaluate the efficacy and cardiac effects of compounds that are tissue selective thyroid hormone agonists. The efficacy endpoints measured are whole body oxygen consumption and the activity of liver mitochrondrial alpha-glycerophosphate dehydrogenase (mGPDH). The cardiac endpoints that are measured are heart weight and heart mGPDH activity. The protocol involves dosing fatty Zucker rats for 6 days, then measuring oxygen consumption and harvesting of tissues for preparation of mitochondria and assaying of enzyme activity.

Male fatty Zucker rats having a body weight range of about 400–500 g are housed at least 3–7d in individual cages under standard laboratory conditions prior to the initiation of the study.

A compound of formula (I) or a pharmaceutically acceptable salt, racemate or enantiomer thereof, vehicle or 3,3'5-triiodo-L-thyronine sodium salt (T3) is administered by oral gavage as a single daily dose given between 3 and 6 p.m. for 6 days. The compound of formula (I), or a pharmaceutically acceptable salt, racemate or enantiomer thereof, or T3 is dissolved in a small volume of 1 NaOH and then brought up to the appropriate volume with 0.01 N NaOH containing 0.25% methyl cellulose (the ratio of 0.01 N NaOH/MC to 1 N NaOH is 10:1). The dosing volume is 1 ml.

Oxygen consumption is measured the day after the last dose of compound is given using an open circuit, indirect calorimeter (Oxymax, Columbus Instruments, 950 North Hague Ave., Columbus, Ohio 43204). The Oxymax gas sensors are calibrated with $N_2$ gas and gas mixture (0.5% $CO_2$, 20.5% $O_2$, 79% $N_2$) before each experiment. Rats are removed from their home cages, their body weights are recorded and they are placed in sealed chambers (43×43×10 cm) of the calorimeter and the chambers are placed in activity monitors. Air flow rate through the chambers is set at 1.6–1.7 l/min. The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis; ambulatory activity is recorded when two consecutive beams are broken and the results are recorded as counts. Oxygen consumption and ambulatory activity are measured every 10 minutes for 5–6.5 hours. Resting oxygen consumption is calculated on individual rats by averaging the values excluding the first 5 values and values obtained during time periods where ambulatory activity exceeds 100 counts.

When evaluated in the experimental protocol described hereinabove utilizing fatty Zucker rats, the compound ethyl N-[4-[3'-[(4-fluorophenyl)hydroxymethyl]-4'-hydroxyphenoxy]-3,5-dimethylphenyl]oxamate (CGS-26214) stimulated oxygen consumption by 14 to 31% at doses of 0.005 to 0.3 mg/kg body weight and the compound N-[3,5-dimethyl-4-(4'-hydroxy-3'-isopropylphenoxy)-phenyl]-oxamic acid (CGS-23425) stimulated oxygen consumption by 27% at a dose of 1.0 mg/kg body weight.

What is claimed is:
1. A method of treating obesity in an animal which comprises administering to an animal in need of such treatment an obesity-treating amount of a compound of the formula:

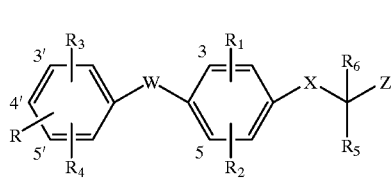

(I)

or a pharmaceutically acceptable salt, racemate or enantiomer thereof, wherein

R is hydroxy, esterified hydroxy or etherified hydroxy;

R and $R_2$ are, independently, halogen, trifluoromethyl or lower alkyl;

$R_3$ is halogen, trifluoromethyl, lower alkyl, lower alkanoyl, garyl, hydroxy-lower alkyl, aryl-lower alkyl, cycloalkyl or cyclo-lower alkyl, carbocyclic aryltmethyl, carbocyclic aroyl, carbocyclic arylhydroxymethyl; or s is the radical:

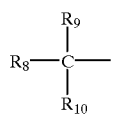

wherein $R_8$ is hydrogen, lower alkyl, aryl, cycloalkyl, aryl-lower alkyl or cycloalkyl-lower alkyl;

$R_9$ is hydroxy or acyloxy; $R_{10}$ is hydrogen or lower alkyl; or $R_9$ and $R_{10}$, taken together with the carbon atom to which they are attached, form a carbonyl group;

$R_4$ is hydrogen, halogen, trifluoromethyl or lower alkyl;

$R_5$ and $R_6$ are, independently, hydrogen or lower alkyl or $R_5$ and $R_6$, taken together with the carbon atom to which they are attached, form a carbonyl group;

X is O, S or —$NR_7$;

$R_7$ is hydrogen or lower alkyl;

W is O or S; and

Z is carboxyl or carboxyl derivatized as a pharmaceutically acceptable ester or amide.

2. A method according to claim 1 which comprises administering a compound of formula (I) or a pharmaceutically acceptable salt, racemate or enantiomer thereof, wherein R is located at the 4'-position, $R_1$ and $R_2$ are located at the 3 and 5 positions and $R_3$ and $R_4$ are located at the 3' and 5'-positions.

3. A method according to claim 1 which comprises administering a compound of formula (I), or a pharmaceutically acceptable salt, racemate or enantiomer thereof, wherein X is O or —$NR_7$; W is O; $R_4$ is hydrogen and Z is carboxy or carboxy derivatized as a pharmaceutically acceptable ester.

4. A method according to claim 1 which comprises administering a compound of the formula:

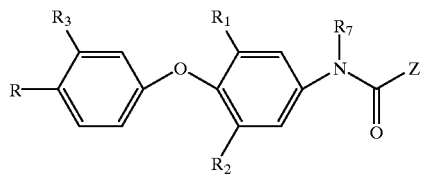

(II)

or a pharmaceutically acceptable salt, racemate or enantiomer thereof wherein,

R is hydroxy, esterified hydroxy or etherified hydroxy;

$R_1$ and $R_2$ are, independently, halogen, trifluoromethyl or ($C_1$–$C_3$) alkyl;

$R_3$ is lower alkyl, lower alkanoyl, hydroxy-lower alkyl, carbocyclic arylmethyl, carbocyclic aroyl or carbocyclic aryl hydroxymethyl;

$R_7$ is hydrogen or lower alkyl; and

Z is carboxyl or carboxyl derivatized as a pharmaceutically acceptable ester or amide.

5. A method according to claim 1 which comprises administering a compound of the formula:

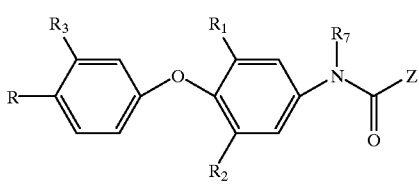

(III)

or a pharmaceutically acceptable salt, racemate or enantiomer thereof wherein,

R is hydroxy, esterified hydroxy or etherified hydroxy;

$R_1$ and $R_2$ are, independently, halogen, trifluoromethyl or ($C_1$–$C_3$) alkyl;

$R_3$ is lower alkyl, carbocyclic aroyl, carbocyclic arylmethyl or carbocyclic aryl hydroxymethyl;

$R_7$ is hydrogen or lower alkyl; and

Z is carboxyl or carboxyl derivatized as a pharmaceutically acceptable ester or amide.

6. A method according to claim 5 which comprises administering a compound of formula (III), or a pharmaceutically acceptable salt, racemate or enantiomer thereof, wherein R is hydroxy, acyloxy, lower alkoxy or tetrahydropyranyloxy.

7. A method according to claim 5 which comprises administering a compound of formula (III), or a pharmaceutically acceptable salt, racemate or enantiomer thereof, wherein R is hydroxy, lower alkanoyloxy, lower alkoxy or tetrahydropyranyloxy; $R_1$ and $R_2$ are the same and are halogen or ($C_1$–$C_3$)alkyl; $R_3$ is ($C_1$–$C_3$)alkyl or monocyclic carbocyclic arylmethyl; $R_7$ is hydrogen or ($C_1$–$C_2$)alkyl and Z is carboxyl or carboxyl derivatized as a pharmaceutically acceptable ester or amide.

8. A method according to claim 5 which comprises administering a compound of formula (III), or a pharmaceutically acceptable salt, racemate or enantiomer thereof, wherein Z is carboxyl or carboxyl derivatized as a pharmaceutically acceptable ester.

9. A method according to claim 5 which comprises administering a compound of formula (III), or a pharmaceutically acceptable salt, racemate or enantiomer thereof, wherein R is hydroxy; $R_1$ and $R_2$ are the same and are chloro or methyl; $R_3$ is isopropyl, benzyl or benzyl substituted by halogen, lower alkyl, lower alkoxy or trifluoromethyl; $R_7$ is hydrogen and Z is carboxyl or lower alkoxycarbonyl.

10. A method according to claim 9 which comprises administering N-[3,5-dimethyl-4-(4'-hydroxy-3'-isopropylphenoxy)-phenyl]-oxamic acid or a pharmaceutically acceptable salt thereof.

11. A method according to claim 9 which comprises administering N-[3,5-dichloro-4-(4'-hydroxy-3'-isopropylphenoxy)-phenyl]-oxamic acid or a pharmaceutically acceptable salt thereof.

12. A method according to claim 5 which comprises administering a compound of formula (III), or a pharmaceutically acceptable salt, racemate or enantiomer thereof, wherein R is hydroxy, lower alkanoyloxy, lower alkoxy or tetrahydropyranyloxy; $R_1$ and $R_2$ are the same and are, independently, halogen or ($C_1$–$C_3$)alkyl; $R_3$ is carbocyclic aroyl or carbocyclic aryl hydroxymethyl; $R_7$ is hydrogen or ($C_1$–$C_2$)alkyl and Z is carboxyl or carboxyl derivatized as a pharmaceutically acceptable ester or amide.

13. A method according to claim 12 which comprises administering a compound of formula (III), or a pharmaceutically acceptable salt, racemate or enantiomer thereof, wherein R is hydroxy; $R_1$ and $R_2$ are the same and are chloro or methyl; $R_3$ is phenyl-hydroxymethyl or phenylhydroxymethyl substituted on phenyl by halogen, lower alkyl, lower alkoxy or trifluoromethyl, or benzoyl or benzoyl substituted by halogen, lower alkyl, lower alkoxy or trifluoromethyl; $R_7$ is hydrogen and Z is carboxyl or lower oxycarbonyl.

14. A method according to claim 13 which comprises administering ethyl N-[4-[3'-[(4-fluorophenyl) hydroxymethyl]-4'-hydroxyphenoxy]-3,5-dimethylphenyl] oxamate or a racemate or enantiomer thereof.

15. A method according to claim 13 which comprises administering N-[4-[3'-[(4-fluorophenyl)hydroxymethyl]-4'-hydroxyphenoxy]-3,5-dimethylphenyl]oxamic acid, or a pharmaceutically acceptable salt, racemate or enantiomer thereof.

16. A method of treating obesity in an animal which comprises administering to an animal in need of such treatment obesity-treating amounts of a compound of the formula:

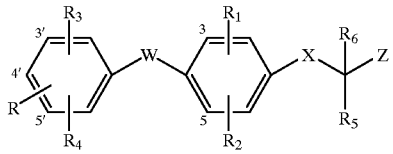

(I)

or a pharmaceutically acceptable salt, racemate or enantiomer thereof, wherein

R is hydroxy, esterified hydroxy or etherified hydroxy;

$R_1$ and $R_2$ are, independently, halogen, trifluoromethyl, or lower alkyl;

$R_3$ is halogen, trifluoromethyl, lower alkyl, aryl, aryl-lower alkyl, cycloalkyl or cycloalkyl-lower alkyl, carbocyclic arylmethyl, carbocyclic aroyl, carbocyclic arylhydroxymethyl; or $R_3$ is the radical:

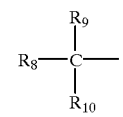

wherein $R_8$ is hydrogen, lower alkyl, aryl, cycloalkyl, aryl-lower alkyl or cycloalkyl-lower alkyl;

$R_9$ is hydroxy or acyloxy; $R_{10}$ is hydrogen or lower alkyl; or $R_4$ and $R_{10}$, taken together with the carbon atom to which they are attached, form a carbonyl group;

$R_4$ is hydrogen, halogen, trifluoromethyl or lower alkyl;

$R_5$ and $R_6$ are, independently, hydrogen or lower alkyl or $R_5$ and $R_6$, taken together with the carbon atom to which they are attached, form a carbonyl group;

X is O, S or —$NR_7$;

$R_7$ is hydrogen or lower alkyl;

W is O or S; and

Z is carboxyl or carboxyl derivatized as a pharmaceutically acceptable ester or amide and an anorectic agent.

17. A method according to claim 16 which comprises administering N-[3,5-dimethyl-4-(4'-hydroxy-3'-isopropylphenoxy)-phenyl]-oxamic acid or a pharmaceutically acceptable salt thereof.

18. A method according to claim 16 which comprises administering N-[3,5-dichloro-4-(4'-hydroxy-3'-isopropylphenoxy)-phenyl]-oxamic acid or a pharmaceutically acceptable salt thereof.

19. A method according to claim 16 which comprises administering ethyl N-[4-[3'-[(4-fluorophenyl) hydroxymethyl]-4'-hydroxyphenoxy]-3,5-dimethylphenyl] oxamate or a racemate or enantiomer thereof.

20. A method according to claim 16 which comprises administering N-[4-[3'-[(4-fluorophenyl)hydroxymethyl]-4'-hydroxyphenoxy]-3,5-dimethylphenyl]oxamic acid, or a pharmaceutically acceptable salt, racemate or enantiomer thereof.

21. A method according to claim 16 wherein said anorectic agent is selected from the group consisting of phenylpropanolamine, ephedrine, pseudoephdrine, phentermine, an NPY antagonist, a CCK-A agonist, a monoamine reuptake inhibitor, a sympathiomimetic agent, a serotoninergic agent, a dopamine agonist, a melanocyte-stimulating hormone receptor agonist or mimetic, a cannabinoid receptor antagonist, a melanocyte-stimulating hormone analog, a melanin concentrating hormone antagonist, leptin, a leptin analog, a galanin antagonist and an orexin receptor antagonist.

22. A method according to claim 21 wherein said anorectic agent is a CCK-A agonist.

23. A method according to claim 21 wherein said anorectic agent is leptin or a leptin analog.

24. A method according to claim 21 wherein said anorectic agent is a galanin antagonist.

25. A method according to claim 21 wherein said anorectic agent is phentermine.

26. A method according to claim 21 wherein said monoamine reuptake inhibitor is sibutramine.

27. A method according to claim 21 wherein said serotoninergic agent is dexfenfluramine or fenfluramine.

* * * * *